(12) United States Patent
Buhl

(10) Patent No.: US 7,704,240 B2
(45) Date of Patent: Apr. 27, 2010

(54) PACKAGE FOR AN OSTOMY APPLIANCE

(75) Inventor: Anne Louise Buhl, Vedbaek (DK)

(73) Assignee: Coloplast A/S, Humlebaek (DK)

( * ) Notice: Subject to any disclaimer, the term of this patent is extended or adjusted under 35 U.S.C. 154(b) by 884 days.

(21) Appl. No.: 10/566,590

(22) PCT Filed: Feb. 4, 2004

(86) PCT No.: PCT/DK2004/000084

§ 371 (c)(1),
(2), (4) Date: Sep. 25, 2006

(87) PCT Pub. No.: WO2004/069113

PCT Pub. Date: Aug. 19, 2004

(65) Prior Publication Data

US 2007/0045300 A1    Mar. 1, 2007

(30) Foreign Application Priority Data

Feb. 4, 2003    (DK) .............................. 2003 00156

(51) Int. Cl.
*A61F 5/44*    (2006.01)
*A61M 1/00*    (2006.01)
(52) U.S. Cl. ....................... 604/332; 604/327
(58) Field of Classification Search ................. 604/322, 604/333–345; 4/300, 420
See application file for complete search history.

(56) References Cited

U.S. PATENT DOCUMENTS

| 5,135,519 | A | 8/1992 | Helmer |
| 5,647,670 | A | 7/1997 | Iscovich |
| 5,755,514 | A | 5/1998 | Baar-Bartelt |
| 7,261,706 | B2 * | 8/2007 | Andersen et al. ............ 604/322 |
| 2004/0147887 | A1 * | 7/2004 | Hagstroem et al. .......... 604/332 |
| 2005/0040060 | A1 | 2/2005 | Andersen et al. |

FOREIGN PATENT DOCUMENTS

| DE | 30 38 923 A1 | 5/1982 |
| DE | 297 03 223 U1 | 5/1997 |
| EP | 0 841 049 A1 | 5/1998 |
| GB | 2 083 762 A | 3/1982 |
| WO | WO 03/022186 A1 | 3/2003 |

\* cited by examiner

*Primary Examiner*—Daniel L Robinson
(74) *Attorney, Agent, or Firm*—Coloplast Corp., Coloplast A/S; Daniel G. Chapik; Nicholas R. Baumann

(57) ABSTRACT

A package for a disposable ostomy receiving bag, said package comprising a first compartment capable of accommodating a (fresh) ostomy receiving bag and a second compartment capable of accommodating a used ostomy receiving bag, said second compartment being sealable so as to confine the receiving bag facilitates the handling of fresh and used bags and renders the user more independent of the availability of a lavatory.

13 Claims, 5 Drawing Sheets

PACKAGE FOR AN OSTOMY APPLIANCE

This is a nationalization of PCT/DK04/000084 filed Feb. 4, 2004 and published in English.

BACKGROUND OF THE INVENTION

Field of the Invention

The present invention relates to a package for a collecting bag to be secured to the abdomen of a patient or to a body side ostomy member for collecting fluids or excretions emerging from an abdominal stoma and the preparation thereof.

In connection with surgery for a number of diseases in the gastro-intestinal or urinary tract a consequence is, in many cases, that the colon, the ileum or the ureter has been exposed surgically and the patient is left with an abdominal stoma, or, in nephrostomy or ureterostomy, the ureter or a catheter is exposed in the back or the chest region or abdominal region, and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma/ureter/catheter. Also in connection with a fistula, the patient will have to rely on an appliance to collect the bodily material emerging from such opening.

Ostomy appliances are well known. Such appliances may be two-piece or one-piece appliances. In both types of appliances, an adhesive barrier member (or base plate) is attached to the wearer's abdomen/back/chest. In case of a one-piece appliance, a receiving member or bag is attached to the base plate. In case of a two-piece appliance, the adhesive barrier member forms part of a body side member and a receiving member or bag is attached releasably to the body side ostomy member for receiving exudates from the stoma.

When using one-piece appliances, the whole appliance, including the adhesive skin barrier securing the appliance to the skin is normally removed and replaced by a fresh appliance. When using two-piece appliances, the body side ostomy member is left in place up to several days, and only the receiving member or bag attached to the body side member is replaced. The attachment means for attaching an ostomy receiving bag may e.g. be a system comprising matching coupling rings or matching flanges and adhesive surfaces engaging with and sealing against a flange area of the body side member.

A known major problem with such receiving bags is that it can be difficult to dispose of the used bag in a convenient and hygienic manner. Some ostomists will cut the used bags open, e.g. by cutting off an edge thereof and deposit the contents into a WC for flushing away and dispose or deposit the empty bag in a waste bin. Such disposal of used bags and the contents therein is indeed unhygienic and unpleasant for the user, and the problems with disposal of a used bag is even more pronounced if the user does not have access to normal toilet facilities, e.g. when travelling.

SUMMARY OF THE INVENTION

The present invention relates to a package for a disposable ostomy receiving bag.

The invention also relates to a method of producing a package for containing a disposable ostomy receiving bag.

The present invention is described with reference to use in connection with an ostomy collecting bag but other uses of the package overcoming corresponding problems are also considered a part of the invention, e.g. the use in connection with handling hygienic articles such as sanitary towels or diapers.

BRIEF DESCRIPTION OF THE DRAWINGS

The invention is disclosed more in detail with reference to the drawings, in which.

DETAILED DESCRIPTION OF THE PRESENT INVENTION

Figure 1:
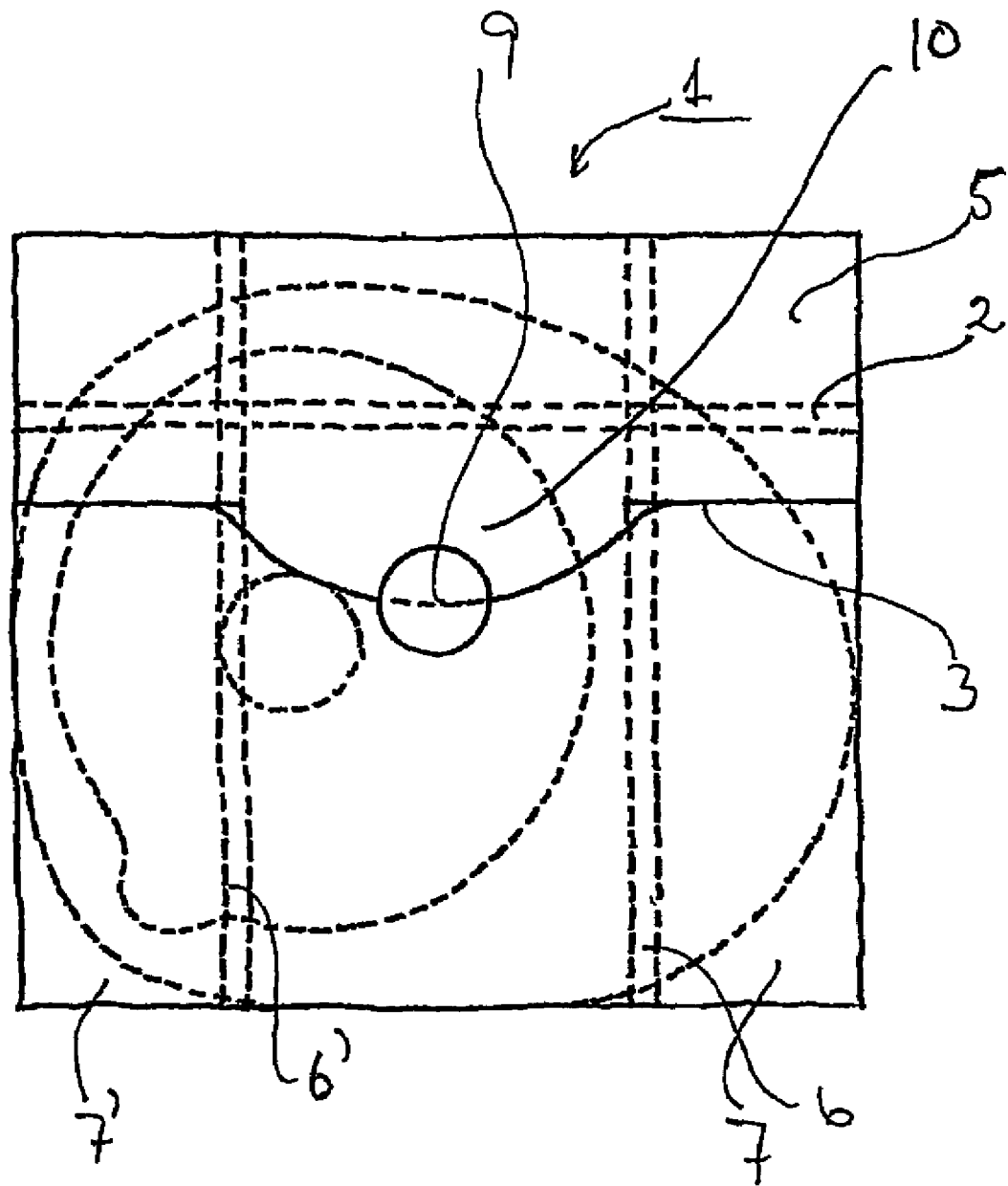
FIG. 1 shows a front view of a package of the invention comprising an ostomy appliance.

The present invention relates to a package for a disposable ostomy receiving bag, said package comprising a first compartment capable of accommodating a (fresh) ostomy receiving bag and a second compartment capable of accommodating a used ostomy receiving bag, said second compartment being sealable so as to confine the receiving bag, wherein the package is in the form of a bag having an open end and a cavity, the cavity defining the second compartment and wherein the bag is folded so as to define the first compartment.

In one embodiment the folded bag defines at least three folded edges.

The bag of the invention facilitates the handling of fresh and used bags and renders the user more independent on immediate availability of a lavatory or toilet facilities when having to substitute a bag while being out of the daily whereabouts. Thus, the invention renders it easy for an ostomate to carry a fresh bag in a discrete manner and also to handle the used bag in a safe and discrete manner reducing the risk of embarrassing situations in case of a leak liberating odour or the contents of the bag. This will increase the chances of living a more normal social life and increase the quality of life of the ostomate.

The package of the invention may be used for receiving bags for both one-piece and two-piece applications.

Suitable materials for a package of the present invention are thin flexible sheet materials, which are moisture resistant and impervious to liquids and preferably also odours, e.g. polyolefins such as polyethylene or polypropylene, EVA, polyvinylidene chloride, or chlorinated polyethylene or copolymers of PE and EVA or combinations of such foils. The walls of the bag may in a special embodiment be laminated with materials conventionally used in the production of ostomy appliances such as non-woven materials of polyethylene, polypropylene or a polyester.

The package for a disposable ostomy receiving bag, is in the form of a bag. The second compartment of the package is constituted by the bag which has an opening defining the entrance of said second compartment. The bag may have a first wall and a second wall of sheet material which could be attached to each other by means of glue, welding or any other suitable means of attachment. When the first and second walls are attached to each other they define the inner surfaces of the cavity and thus the inner walls of the second compartment.

Seen from one side the bag may have any shape such as rectangular, triangular or any other polygonal shape or e.g. a semi-circle. The circumference of the opening may be larger than the circumference of any other part of the cavity. In another embodiment the circumference of the opening is smaller than the circumference of at least a part of the cavity.

In order to define the first compartment the bag is folded. When the bag, and thereby the second compartment, is defined by a first and second wall, the inner surfaces of the first compartment is defined by the outer surface of the first wall. Seen from the patient/skin side of the package the order of the materials/compartments may thus be 1) second wall 2) second compartment 3) first wall 4) first compartment 5) first wall (first folded part)

6) second wall (first folded part)

if the folded slips overlap each other the following is furthermore added to the order of the materials 7) first wall (second folded part)

8) second wall (second folded part)

as 5) and 6) defines one slip and 7) and 8) the other slip.

A suitable embodiment of a package is in the form of a bag having a closed end and an open end and having a first wall and a second wall, said bag having edges connecting the closed and open ends of the bag wherein the edges are folded so as to cover each a longitudinal strip of the first wall, said bag also being folded so that the closed end of the first wall is parallel to the open end of the first wall to form the first compartment. To prevent a fresh ostomy appliance confined by the first compartment from falling out, the opposing sides of the first wall may be connected with releasable adhesive dots or a releasable label may be applied across the opening of the first chamber. In this embodiment, a relatively large bag which may accommodate a used bag with contents is also rendered suitable for accommodating a fresh receiving bag and, at the same time, ensures as high a degree of discretion as it may e.g. be carried in a hand bag or a pocket. It is preferred that the material for a package of the invention is opaque for blurring the contents for improving the discretion when it is necessary to carry the package containing a used bag. Furthermore, the bag is easy to unfold without risk of damaging the walls of the bag compromising the later use for carrying the used bag.

It is preferred that the closed end of the bag, in its folded position, leaves a part of the open end of the bag free as a flap capable of covering the inlet opening of the compartment when folded as this flap will protect a fresh bag against mechanical damage when stowed in a hand bag or a pocket.

In accordance with another preferred embodiment, one of the walls of the open end of the bag (the one being at the outside after folding the bag) is extended beyond the edge of the other wall forming an extended flap, which may have a general rectangular, triangular or oval shape or the shape of a part of a circle.

The safety against damage and unintended catching of the bag is increased when the flap and the outer surface of the second wall forming the first compartment are provided with means for releasable attachment of the flap to the surface of the wall. Such means may be a releasable adhesive sealing or a peelable weld seam. The sealing of the first compartment may preferably be effected using an adhesive label placed on the flap. Such a label may also be used in a manner known per se for carrying information identifying the product.

Due to the stiffness of the double folding and the supporting effect of the ostomy appliance, an unintended unfolding of the bag and opening of the first compartment and uncovering the ostomy appliance may be ensured alone by applying an adhesive label without having to rely on further sealing of the package of the invention.

The second compartment of the package is advantageously sealed by tying a knot on a part of the open end or using another suitable sealing means such as a clamp known per se for sealing an ostomy bag or an adhesive sealing which is preferably covered by a protecting release liner made from a suitable material such as polyethylene or a siliconised paper to be removed before use or a reusable adhesive placed on the flap. When a reusable adhesive is used on the flap for closing the first compartment, this may also be used for closing the second compartment in which the used receiving bag is then safely confined.

The package may be made from a bag made from a thermoplastic material in a manner known per se. It is preferred that the edges are folded so as to cover each a longitudinal strip of the first wall having a width of from 15% to 50% of the total width of the bag, preferably from 25% to 40% of the total width of the bag, e.g. from 30% to 35% which together with the stiffness of the ostomy appliance will be sufficient to prevent an unintended unfolding of the bag and opening of the first compartment and uncovering the ostomy appliance when sealing the first compartment using an adhesive label.

A safe and discrete depositing of the used bag when having to rely on using a waste bin is secured when the bag is made from a material being substantially impervious to odour. A suitable such material is a material conventionally being used for production of ostomy appliances, e.g. the ones mentioned above.

In another (second) aspect the invention relates to a method of producing a package containing a disposable ostomy receiving bag, said package comprising a first compartment capable of accommodating a (fresh) ostomy receiving bag and a second compartment capable of accommodating a used ostomy receiving bag, said second compartment being sealable so as to confine the receiving bag, said method comprising placing an ostomy appliance on a bag having a closed end and an open end and having a first wall and a second wall and said bag having edges connecting the closed and open ends of the bag wherein the edges are folded so as to cover each a longitudinal strip of the first wall and a part of the ostomy appliance, and subsequently folding the closed end of the first wall of said bag so that is parallel to the open end of the first wall and covers the folded strips and the ostomy appliance to form the first compartment.

The package of the second aspect may be in the form as described in claim 1 wherein the wherein the package is in the form of a container bag having an open end and a cavity, the cavity defining the second compartment and wherein the container bag is folded so as to define the first compartment. The package may be folded such that the edges of the closed end and the open end are not necessarily parallel but may be transverse to each other. However it is essential that the package is folded so as to define the first compartment.

It is preferred that the bag is folded so that the closed end of the bag, in its folded position, leaves a part of the open end of the bag free as a flap which is then folded to cover the inlet opening of the first compartment.

In a preferred embodiment, the flap is then secured to the outer surface of the second wall for closing the first compartment by means for releasable attachment of the flap to the surface of the wall.

DESCRIPTION OF THE PREFERRED EMBODIMENTS

The invention is now explained more in detail with reference to the drawings showing preferred embodiments of the invention.

Figure 2:
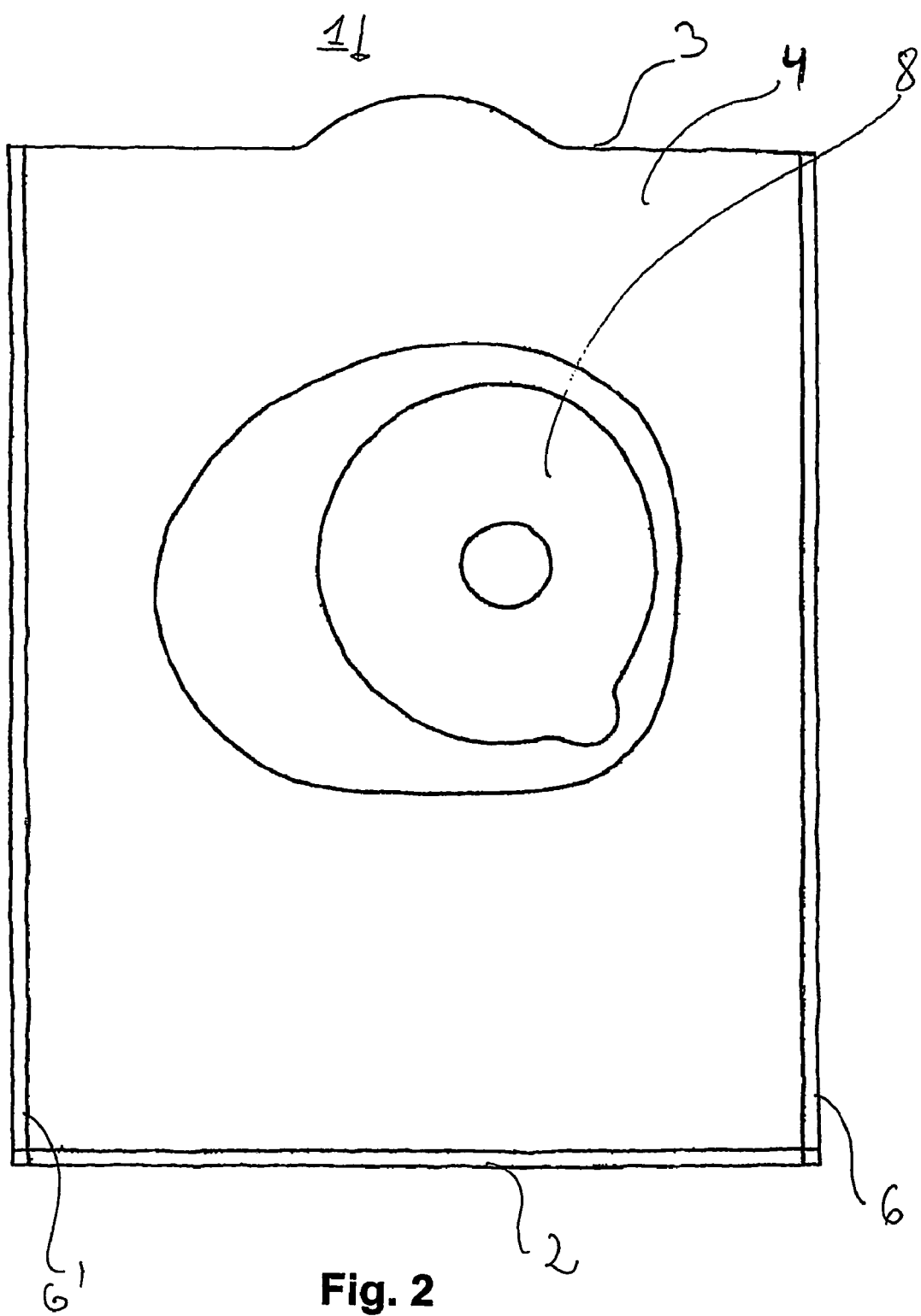
FIG. 2 shows a first stage in a process for preparing a package of the invention containing an ostomy appliance.
Figure 3:
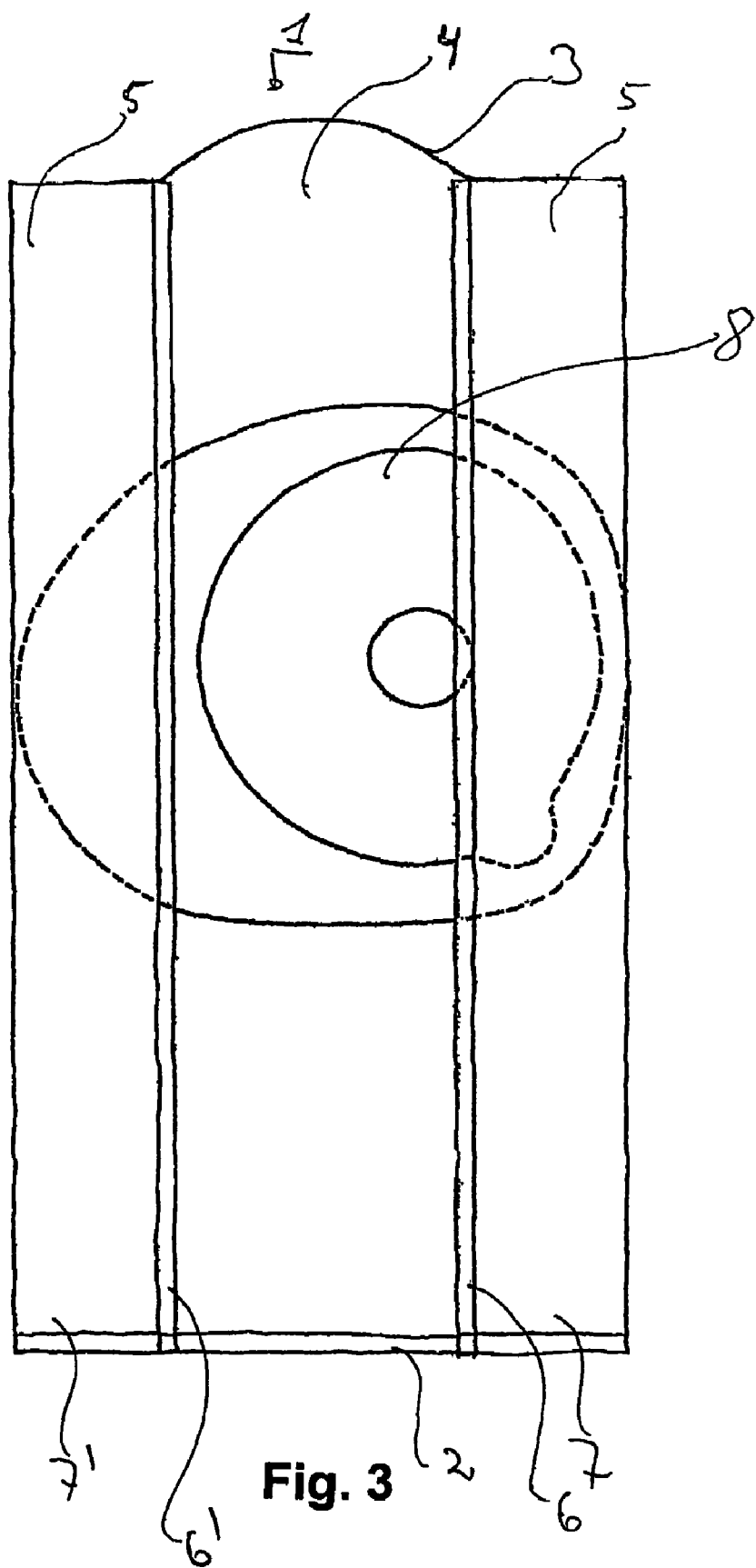
FIG. 3 shows a second stage in a process for preparing a package of the invention containing an ostomy appliance.
Figure 4:
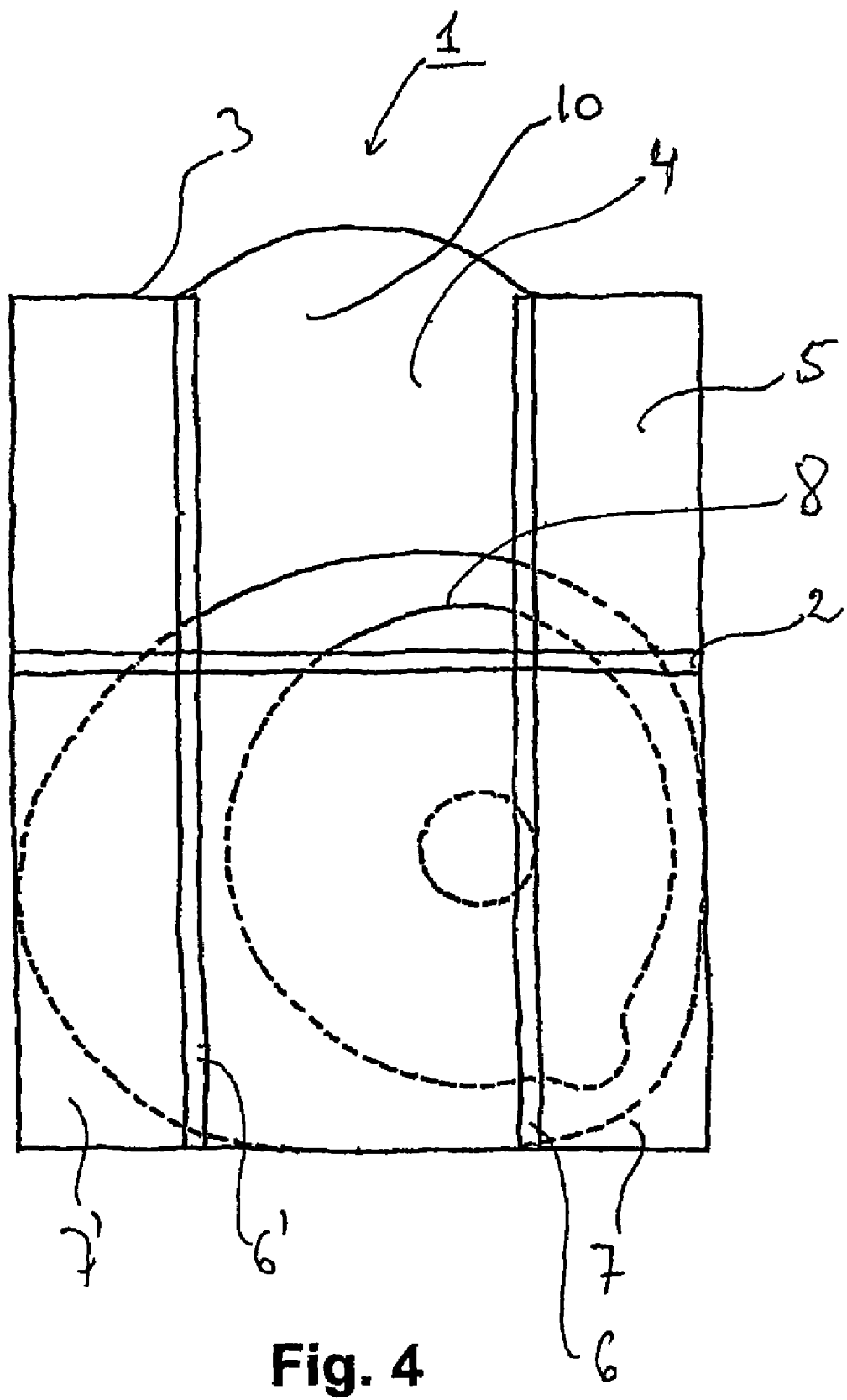
FIG. 4 shows a third stage in a process for preparing a package of the invention containing an ostomy appliance.

Reference is made to FIGS. 1 and 4 showing a front view of an embodiment of a package of the invention is in the form of a bag 1 having a closed 2 end and an open end 3 and having a first wall 4 and a second wall 5 and said bag having edges 6,6' connecting the closed and open ends of the bag wherein the edges are folded so as to cover each a longitudinal strip 7,7' of the first wall, said bag subsequently being folded so that the closed end of the first wall is parallel to the open end of the first wall to form the first compartment. The first compartment comprises an ostomy appliance 8 and is open in FIG. 3 and closed in FIG. 4 in which the first compartment is also sealed using an adhesive label 9. FIGS. 2 and 3 show stages one and two in a process for preparing a package of the invention comprising an ostomy appliance, FIG. 4 showing a third stage and FIG. 1 the finished package.

In a method of producing a package of the invention containing a disposable ostomy receiving bag, said package comprising a first compartment capable of accommodating a (fresh) ostomy receiving bag and a second compartment capable of accommodating a used ostomy receiving bag, said second compartment being sealable so as to confine the receiving bag, said method comprising in a first stage placing an ostomy appliance 8 on a bag 1 having a closed end 2 and an open end b and having a first wall 4 and a second wall 5 and said bag having edges 6,6' connecting the closed 2 and open 3 ends of the bag wherein the edges 6,6' are folded so as to cover each a longitudinal strip 7,7' of the first wall 4 and a part of the ostomy appliance 8, and then folding the closed end 2 of the first wall 4 of said bag so that is parallel to the open 3 end of the first wall and covers the folded strips and the ostomy appliance leaving the upper end of the bag forming a flap 10 to form the first compartment. Then, the first compartment closed by folding the flap 10 so that the first wall contacts the outer surface of the second wall 5, said compartment encasing an indicated ostomy receiving bag 8, the outer surface of the second wall and further being provided with an adhesive label 9 for closing the first compartment When using the package of the invention, the ostomate breaks the seal of the flap, opens the first compartment and removes the fresh ostomy receiving bag for substituting the one in use. Then, the first compartment of the bag is unfolded giving access to the full space of the package forming the second compartment. After detaching the used receiving bag from the abdomen or from an ostomy body side member, the bag may be placed in the second compartment with or without emptying the bag as is appropriate. Then the package is advantageously sealed by tying a knot on a part of the open end or using another suitable sealing means such as a clamp known per se for sealing an ostomy bag or an adhesive sealing which is preferably covered by a protecting release liner made from a suitable material such as polyethylene or a siliconised paper to be removed before use or a reusable adhesive placed on the flap. When a reusable adhesive is used on the flap, this may also be used for closing the second compartment in which the used receiving bag is then safely confined.

Figure 5:
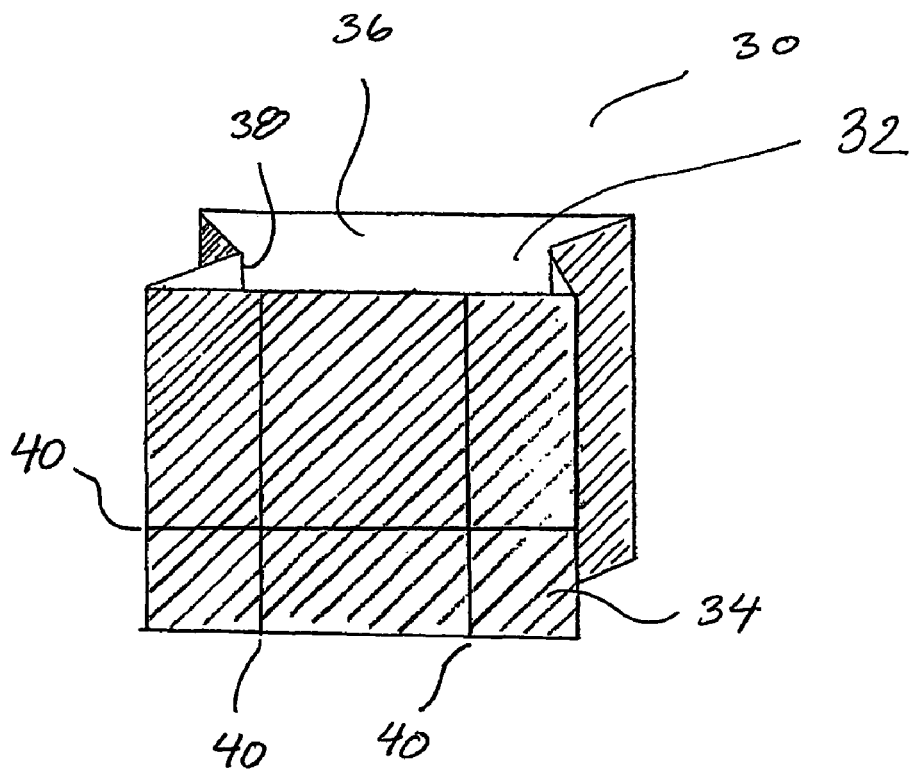
FIG. 5 shows an alternative way of folding the package.

In FIG. 5 is seen a package 30 folded prior to the folding process which defines the first compartment (not shown as the package in this figure is not folded according to claim 1) which is next to second compartment 32. The package comprises a first wall 34 and a second wall 36 which are attached to each other along an edge 38. Prior to the folding according to claim 1, the edges 38 are folded in inwards such that the area of the first wall 34 and the second wall 36 visually seems to be smaller, as a part of the walls are hidden inside the bag. Edges on the sides and/or the bottom may be folded this way.

Afterwards the package is folded as described previously such that the lines 40 becomes the outer edges of the package in the folded state.

Figure 6:
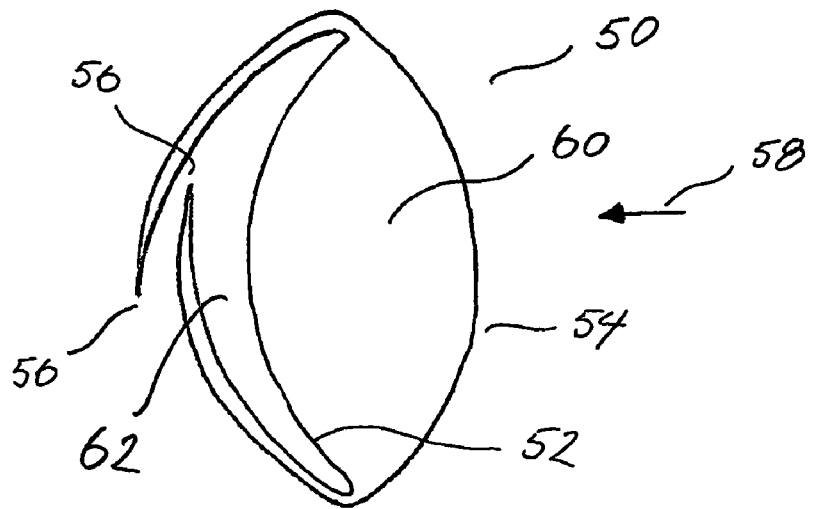
FIG. 6 shows a cross-sectional view of the package folded according to the present invention.

FIG. 6 shows a cross-sectional view of the bag folded according to the present invention. The bag 50 comprises a first wall 52 and a second wall 54 attached to each other in edges 56. The order of materials/compartments along the direction indicated by arrow 58 is 1) second wall 54

2) second compartment 60

3) first wall 52

4) first compartment 62

5) first wall (first folded part) 52

6) second wall (first folded part) 54

7) first wall (second folded part) 52

8) second wall (second folded part) 54

The invention claimed is:

1. A package comprising a ostomy receiving appliance and a bag for disposing a used ostomy receiving appliance, the bag defining a longitudinal axis and a first compartment and a second compartment, the bag having an open end and a cavity extending to a closed end, the cavity defining the second compartment which is sealable so as to confine the used ostomy receiving appliance, wherein a first lateral edge of the bag extending between the open and closed ends is folded toward the longitudinal axis and a second opposing lateral edge of the bag extending between the open and closed ends is folded toward the longitudinal axis, the first lateral edge and the second lateral edge folded one adjacent to an other so as to define the first compartment and wherein the ostomy receiving appliance is accommodated in the first compartment.

2. A package according to claim 1, wherein the folded bag defines at least three folded edges.

3. A package as claimed in claim 1, wherein the bag has a first wall and a second wall and edges connecting a closed end and the open end of the bag, wherein the edges are folded so as to cover each a longitudinal strip of the first wall, said bag subsequently is folded so that the closed end of the first wall is parallel to the open end of the first wall to form the first compartment.

4. A package as claimed in claim 1, wherein the closed end of the bag, in its folded position, leaves a part of the open end of the bag free as a flap capable of covering the inlet opening of the compartment.

5. A package as claimed in claim 4, wherein the flap and the outer surface of the second wall forming the first compartment are provided with means for releasable attachment of the flap to the surface of the wall.

6. A package as claimed in claim 1, wherein the bag is made from a material being substantially impervious to odour.

7. A package as claimed in claim 2, wherein the bag has a first wall and a second wall, wherein the first and second lateral edges are folded so as to cover each a longitudinal strip of the first wall, said bag subsequently is folded so that the closed end of the first wall is parallel to the open end of the first wall to form the first compartment.

8. A package as claimed in claim 2, wherein the closed end of the bag, in its folded position, leaves a part of the open end of the bag free as a flap capable of covering the inlet opening of the compartment.

9. A package as claimed in claim 3, wherein the closed end of the bag, in its folded position, leaves a part of the open end of the bag free as a flap capable of covering the inlet opening of the compartment.

10. A method of producing a package comprising a ostomy receiving appliance and a bag for disposing a used ostomy receiving appliance, the bag defining a first and a second compartment, the bag having an open end and a cavity and a first wall and a second wall and edges connecting a closed end and the open end of the bag, wherein the edges are folded so as to cover each a longitudinal strip of the first wall and a part of the ostomy receiving appliance, the cavity defining the second compartment which is sealable so as to confine the used ostomy receiving appliance, the bag being folded so as to define the first compartment and the ostomy receiving appliance being accommodated in the first compartment, the method comprising the steps of:

placing an ostomy receiving appliance on a bag, and folding the closed end of the first wall of the bag so that the closed end is parallel to the open end of the first wall and covers the folded longitudinal strips to form the first compartment.

11. A method as claimed in claim 10, wherein the closed end of the bag, in its folded position, leaves a part of the open end of the bag free as a flap which is then folded to cover the inlet opening of the first compartment.

12. A method as claimed in claim 10, wherein the flap is secured to the outer surface of the second wall for closing the first compartment by means for releasable attachment of the flap to the surface of the wall.

13. A method as claimed in claim 11, wherein the flap is secured to the outer surface of the second wall for closing the first compartment by means for releasable attachment of the flap to the surface of the wall.

* * * * *